United States Patent [19]

Russell-Jones et al.

[11] Patent Number: 6,159,502
[45] Date of Patent: Dec. 12, 2000

[54] ORAL DELIVERY SYSTEMS FOR MICROPARTICLES

[75] Inventors: Gregory John Russell-Jones, Middle Cove; Steven William Westwood, Ashfield, both of Australia

[73] Assignee: Biotech Australia Pty LTD, East Roseville, Australia

[21] Appl. No.: 07/956,003

[22] PCT Filed: Apr. 2, 1992

[86] PCT No.: PCT/AU92/00141

§ 371 Date: Nov. 30, 1992

§ 102(e) Date: Nov. 30, 1992

[87] PCT Pub. No.: WO92/17167

PCT Pub. Date: Oct. 15, 1992

[30] Foreign Application Priority Data

Dec. 2, 1991 [AU] Australia ................................ PK5385

[51] Int. Cl.$^7$ ............................................... A61K 9/14
[52] U.S. Cl. .................... 424/489; 424/491; 424/499; 514/52; 514/21
[58] Field of Search .................... 424/450, 489, 424/491, 499; 428/402.2; 436/829

[56] References Cited

U.S. PATENT DOCUMENTS

| | | | |
|---|---|---|---|
| 2,446,974 | 8/1948 | Chow | 260/117 |
| 2,530,416 | 11/1950 | Wolf | 167/81 |
| 2,576,932 | 12/1951 | Garibaldi et al. | 195/96 |
| 2,595,499 | 5/1952 | Wood et al. | 194/114 |
| 2,646,386 | 7/1953 | Miner et al. | 167/81 |
| 2,709,669 | 5/1955 | Shafer et al. | 167/81 |
| 2,764,521 | 9/1956 | Leviton | 167/81 |
| 2,796,383 | 6/1957 | Robinson | 195/114 |
| 2,823,167 | 2/1958 | Newmark | 167/81 |
| 2,835,627 | 5/1958 | Conine et al. | 167/81 |
| 2,850,491 | 9/1958 | Brenner | 260/112 |
| 2,892,754 | 6/1959 | Lens et al. | 167/74 |
| 2,917,436 | 12/1959 | Baker et al. | 195/125 |
| 3,042,588 | 7/1962 | Heathcote | 195/80 |
| 3,459,855 | 8/1969 | Thuillier | 424/201 |
| 3,920,631 | 11/1975 | Molteni et al. | 260/211.7 |
| 3,981,863 | 9/1976 | Niswender et al. | 536/25 |
| 4,133,951 | 1/1979 | Charlton et al. | 536/25 |
| 4,209,614 | 6/1980 | Bernstein et al. | 536/25 |
| 4,235,866 | 11/1980 | Thoma | 424/1 |
| 4,360,358 | 11/1982 | Sharma | 23/230 B |
| 4,364,939 | 12/1982 | Autissier et al. | 424/180 |
| 4,454,125 | 6/1984 | Demopoulos | 424/201 |
| 4,465,775 | 8/1984 | Houts | 436/503 |
| 4,508,832 | 4/1985 | Carter et al. | 436/517 |
| 4,746,508 | 5/1988 | Carey et al. | 424/88 |
| 4,751,285 | 6/1988 | Toohey | 530/331 |
| 4,839,175 | 6/1989 | Guo | 424/450 |
| 4,952,995 | 8/1990 | Phillips et al. | 357/24 |

FOREIGN PATENT DOCUMENTS

| | | |
|---|---|---|
| 79929/87 | 4/1988 | Australia . |
| 496632 | 10/1953 | Canada . |
| 0 036 277 | 9/1981 | European Pat. Off. . |
| 0 220 030 | 10/1986 | European Pat. Off. . |
| WO 86/06635 | 11/1986 | European Pat. Off. . |
| WO 90/04963 | 5/1990 | European Pat. Off. . |
| 2111895 | 9/1972 | France . |
| 2546474 | 4/1977 | Germany . |
| 467277 | 2/1969 | Switzerland . |
| 665485 | 1/1952 | United Kingdom . |
| 1123853 | 8/1968 | United Kingdom . |
| 1152461 | 5/1969 | United Kingdom . |
| 1345327 | 1/1974 | United Kingdom . |
| 2 146 525 | 4/1985 | United Kingdom . |
| 88/00474 | 1/1988 | WIPO . |
| 88/07365 | 10/1988 | WIPO . |
| 89/08449 | 9/1989 | WIPO . |

OTHER PUBLICATIONS

Kinter, et al., "Atoradiographic Study of Sugar and Amino Acid Absorption by Everted Sacs of Hamster Intestine", *The Journal of Cell Biology*, vol. 25: 19–39 (1965).

Matthews, et al., "Progress in Gastroenterology: Peptide Absorption", *Gastroenterol*, vol. 71:151–161 (1976).

Alpers, Uptake and Fate of Asorbed Amino Acids and Peptides in the Mammalian.

Steinhardt et al., "Kinetics and Charcteristics of Absorption from an Equimolar Mixture of 12 Glycyl–Dipeptides in Human Jejunum", *Gastroenterology*, 90:577–582 (1986).

Sleisenger etal., "Amino Acid Concentrations in Portal Venous Plasma During Absorption a Partial Enzymic Hydrolysate of Casein", *Clinical Science and Molecular Med.*, 52:259–267.

Chung et al., "Protein Digestion and Absorption in Human Small Instestine", *Gastroenterology*, vol. 76, No. 6 (1979).

Adibi et al., "Peptide Absorption and Hydrolysis", *Physiology of the Gastrointestinol Tract* (1981).

Gruber et al., "Some Biological Issues in Oral, Controlled Drug Delivery", *Advanced Drug Delivery Reviews I*, pp. 1–18 (1987).

Bloom et al., "Receptor–Mediated Endocytosis: Review and Overview", *The Mount Sinai Journal of Medicine*, vol. 49, No. 5 (1981).

Elsenhans et al., "Influence of Metal Substitution on Vitamin B12 Binding to Human Intrinsic Factor and Transcobalamins I and II", *Biochemistry*, 23:805–808 (1984).

Alert, *Heterocyclic Chemistry*, p. 148 (1959).

Laurence, "A Potentiometric Study of the Ferric Thiocyanate Complexes", *Trans. Faraday Soc.*, 52:236–242.

Wallenfels etal., "Das Dissoziationsverhalten Von Cystein und Verwandten Shberbindungen", *Biochemische Zeitschrift*, 346:119–132 (1966).

Reichlin. Methods in Enzymol. 70, 1980.

*Primary Examiner*—Gollamudi S. Kishore
*Attorney, Agent, or Firm*—Foley & Lardner

[57] ABSTRACT

There are disclosed complexes and compositions for oral delivery of a substance or substances to the circulation or lymphatic drainage system of a host. The complexes of the invention comprise a microparticle coupled to at least one carrier, the carrier being capable of enabling the complex to be transported to the circulation or lymphatic drainage system via the mucosal epithelium of the host, and the microparticle entrapping or encapsulating, or being capable of entrapping or encapsulating, the substance(s). Examples of suitable carriers are mucosal binding proteins, bacterial adhesins, viral adhesins, toxin binding subunits, lectins, Vitamin $B_{12}$ and analogues or derivatives of Vitamin $B_{12}$ possessing binding activity to Castle's intrinsic factor.

15 Claims, No Drawings

ORAL DELIVERY SYSTEMS FOR MICROPARTICLES

TECHNICAL FIELD

The present invention relates to complexes and compositions for oral delivery of a substances) to the circulation or lymphatic drainage system of a host. The invention also relates to processes for the production of complexes and compositions for oral delivery of a substances) to the circulation or lymphatic drainage system of a host. The invention further relates to a method of delivering a substances) to the circulation or lymphatic drainage system of a host. In addition the invention relates to kits for preparing complexes for oral delivery of a substances) to the circulation or lymphatic drainage system of a host.

BACKGROUND ART

A number of clinical conditions of vertebrates have sufficiently deleterious effects upon the vertebrate to warrant the administration of some pharmaceutically active agent. Such agents may include (i) vaccines, to protect against diseases such as tetanus, diptheria or whoophing cough, (ii) hormones, e.g. insulin, LHRH, vasopressin, oxytocin, or (iii) drugs, e.g. anti-cancer agents, antibiotics. In these cases, a suitable agent is administered to the vertebrate to invoke immunity, to supplement hormone levels, to eliminate the disease causing agent or to provide a therapeutic effect.

Administration of the pharmaceutical to the vertebrate may be via a number of routes including intramuscular (i.m.), subcutaneous (s.c.), or oral (per os, p.o.) administration. I.m. or s.c. administration of the pharmaceutical suffers from the disadvantages that: relatively specialized skills are required to administer the pharmaceutical; large scale administration may be difficult to perform; it is expensive; and a number of side reactions can occur to the agent being administered. For these reasons oral administration of the pharmaceutical is generally preferred. Many antibiotics (tetracycline, penicillin etc), and hormones (progesterone, oestrogen etc) can be successfully administered via the oral route. There are however drugs, hormones and immunogens whose efficacy is almost totally lost upon oral administration (including Calcitonin, Erythropoetin, Granulocyte Colony Stimulating Factor, Stem Cell Factor, Granulocyte Colony Stimulating Factor, LHRH analogues, Somatostatin, Insulin, Interferons, Plasminogen Activator Inhibitors and species of DNA and RNA). This loss of efficacy may be due either to the inability of the intestinal mucosa to absorb these compounds or the breakdown of these substances by various physiological agents in the intestinal milieu. To some extent this effect can be overcome by the administration of extremely large doses of the pharmaceutical agent. This approach, however, is not economically feasible for many pharmaceutical agents.

In an attempt to overcome the problem of degradation a number of encapsulation methods have been employed which enable the encapsulated material to by-pass both the gastric acidity and the pepsin mediated proteolysis encountered within the lumen of the stomach. Typically these methods have involved enteric coated capsules, which only release their contents upon contact with the higher pH of the upper duodenum and jejunum. While this has greatly increased the oral efficacy of a number of compounds, still many substances are pharmaceutically inactive upon oral delivery and must be administered parenterally. Notable examples of such compounds include Calcitonin, Erythropoietin, Granulocyte Colony Stimulating Factor, Stem Cell factor, Granulocyte Macrophage Colony Stimulating Factor, Somatostatin, Insulin, LHRH and its analogues, Interferons, Plasminogen Activator Factor, species of DNA and RNA, and many vaccines.

In a further extension of the encapsulation process, several new forms of encapsulation have been designed in recent years with the specific purpose of trapping large quantities of pharmaceuticals in subcellular capsules, in the hope that once protected from the intestinal milieu, the capsules would themselves be taken up from the intestine and release their contents systemically. Two basic forms of these capsules have been developed, nanocapsules (or microcapsules) and nanospheres (or microspheres). In essence these particles can be formed by one of a number of methods, several of which are outlined below:

(i) Solvent Evaporation

In which a compound which is soluble in one solvent is dispersed into a non-miscible solvent and the first solvent is evaporated off. Particles formed in this fashion have been used to administer (parenterally) a number of water insoluble compounds. An example of such a system would be the formation of polyalkylcyanoacrylate nanocapsules in which the antifungal agent, griseofulvin is entrapped.

(ii) Desolvation

In this method a compound is contained in a liquid in which it is soluble (the solvent) and a second liquid (which is miscible with the first liquid, but in which the compound is not soluble) is added to the solvent. As more of the second liquid is added the compound becomes desolvated. During the process of desolvation the compound rich phase (the coacervate) contains an enriched amount of compound which is dispersed as microdroplets in the compound deficient phase. At this stage the coalesced material can be chemically crosslinked by a suitable crosslinking agent to form micro or nano-particles.

Nanoparticles of gelatin or BSA can be prepared in this way. Solutions of these proteins are desolvated by the addition of sodium sulfate, or ammonium sulfate solutions. At the point of desolvation there is an increase in turbidity, which time the nanoparticles can be formed by the addition of a suitable cross-linker such as glutaraldehyde or butanedione.

(iii) Complex coacervation

In this procedure two polyelectrolytes having opposite charge are mixed in aqueous medium so that a spontaneous liquid/liquid phase separation occurs. The phenomenon is limited to polymers having a suitable ionic charge density and chain length. Typically these microspheres are formed by the addition of a polyanion such as Gum Arabic, Alginate, or Polyphosphate, to a polycation such as Gelatin.

(iv) Polymer/polymer incompatablity

This procedure is based upon the observation that two chemically different polymers dissolved in a common solvent are usually incompatible. Thus the mixture will tend to form two phases. The insoluble phase can be used to coat core particles to form microcapsules. An example would be the precipitation of ethyl cellulose from cyclohexane by the addition of polyethylene.

(v) Interfacial Polymerization

In this technique, two reactants, each dissolved in a mutually immiscible liquid, diffuse to the interface between the two liquids where they react to form a capsule wall. An example of such capsule formation would occur if a mixture of Sebacoyl chloride dissolved in an oil phase was emulsified into an aqueous phase containing ethylenediamine.

Oppenheim and coworkers (1982) have used the desolvation process (described above) to prepare insulin nanoparticles. These nanoparticles were found to be highly effective when administered intravenously, however a disappointingly small quantity of insulin was delivered to the systemic circulation when these particles were given orally. It would appear, from this work that although it was possible to protect the insulin from degradation in the intestine it was not possible to target the nanoparticles to the intestinal mucosa in such a way as to cause uptake. The lack of a suitable targetting agent has in fact rendered this type of microencapsulation technique to be generally unsuitable for oral delivery of encapsulated agents.

Recent work in part undertaken by one of the current inventors (WO086/06635 and PCT/AU86/00299, the disclosures of which are incorporated herein by reference) has, however, provided such a targetting mechanism. In this work use was made of two natural uptake mechanisms in the gut. The first mechanism utilizes the natural uptake mechanism for Vitamin $B_{12}$. During this uptake Vitamin $B_{12}$ firstly binds to intrinsic factor (IF) in the upper small intestine. The Vitamin $B_{12}$-IF complex then passes down the small intestine and binds to an IF receptor located on the surface of the ileal epithelium. The whole Vitamin $B_{12}$-IF-receptor complex is then internalized by receptor-mediated endocytosis and some time later the Vitamin $B_{12}$ appears in the serum. It has been shown that it is possible to chemically link peptides to Vitamin $B_{12}$ in such a manner that does not interfere with its complexing to IF, and to deliver these molecules to the circulation following oral administration. The use of Vitamin $B_{12}$ as a carrier for the oral delivery of active substances is described in PCT/AU86/00299.

In the second mechanism, natural mucosal binding proteins were employed to target various haptens and protein molecules to the gastrointestinal mucosa and elicit their uptake. These binding proteins included bacterial adhesins (987P and K99 pili), a viral adhesin (flu virus), a toxin binding subunit (LTB), as well as a number of plant lectins. This class of molecules was termed carrier molecules.

Both the above described mechanisms do however suffer from the disadvantage that the amount of material which could be delivered through either uptake mechanism was directly proportional to the amount of targetting agent which could be taken up. In this regard, the vitamin $B_{12}$ uptake mechanism is limited by the absolute quantity of Vitamin $B_{12}$ which is normally absorbed, which in most animals amounts to only a few micrograms.

Furthermore, in order for either carrier system to work effectively the conjugated material (hormone, peptide or drug) must preferably be able to survive the proteolytic environment of the small intestine and must also contain a suitable site for chemical cross-linkage to the carrier. During the conjugation, care must be taken to preserve the pharmacological activity of the active agent both during the conjugation as well as in the final complex. Furthermore, a number of peptides may not be suitable for oral delivery (due to sensitivity to proteolysis, or due to lack of suitable functional groups for conjugation) and so new analogues may need to be developed which possess an appropriate conjugation site or have been designed to resist proteolytic degradation. In this respect the present invention can be distinguished from the previous inventions described above in that the carrier molecule of the present invention is not covalently conjugated to the pharmaceutically active agent, but rather the carrier molecule is either covalently linked to the material/polymer comprising the microsphere, or is associated hydrophobically with the surface of the microsphere during its formation.

Surprisingly, the present inventors have discovered that it is possible to prepare complexes comprising at least one carrier molecule and at least one microparticle comprising an active pharmaceutical agent. More surprisingly, the present inventors have discovered that the carrier in such complexes can enable the complex comprising a relatively large microparticle to be transported to the circulatory or lymphatic drainage system via the mucosal epithelium of a host. Thus, the present invention overcomes the above-described disadvantages of the methods of oral delivery of the prior art, since in the complexes of the present invention the active agent is not chemically modified and its physiological activity is preserved while the microparticle provides a protection against degradation or modification in the gastro-intestinal environment. Furthermore, the microparticles of the invention are linked to a carrier molecule which can specifically target the microparticles to the intestinal epithelium and provoke uptake.

Other advantages of the present invention will be apparent from the objects of the invention and the disclosure of the invention hereinbelow.

OBJECTS OF INVENTION

Objects of this invention are to provide complexes and compositions for oral delivery of a substance(s) to the circulation or lymphatic drainage system of a host.

Other objects are to provide processes for the production of complexes and compositions for oral delivery of a substance(s) to the circulation or lymphatic drainage system of a host, a method of delivering a substance(s) to the circulation or lymphatic drainage system of a host and kits for preparing complexes for oral delivery of a substance(s) to the circulation or lymphatic drainage system of a host.

DISCLOSURE OF INVENTION

The term "carrier" as used throughout the specification includes mucosal binding proteins, Vitamin $B_{12}$, and analogues or derivatives of Vitamin $B_{12}$ possessing binding activity to Castle's intrinsic factor, and also includes within its meaning the expression "carrier molecule".

The term microparticle as used throughout the specification includes microspheres and microcapsules and refers a small particle ranging in size from 1 nanometer to 100 micrometers in diameter.

According to a first embodiment of this invention there is provided a complex for oral delivery of a substance to the circulation or lymphatic drainage system of a host, comprising:

a microparticle coupled to at least one carrier;

the carrier being capable of enabling the complex to be transported to the circulation or lymphatic drainage system via the mucosal epithelium of the host;

the microparticle entrapping or encapsulating the substance whereby the substance is substantially unaffected by intestinal digestive substances of the host; and the microparticle being adapted to release the entrapped or encapsulated substance into the circulation or lymphatic drainage system of the host.

A particularly desired form of the complex of the first embodiment of the present invention is a microsphere or microcapsule coupled to a carrier molecule, the microsphere or microcapsule enclosing a hormone, drug, immunogen, or DNA or RNA (such as ribozyme) component, molecule or analogues thereof, wherein the carrier molecule is a mucosal binding protein or Vitamin $B_{12}$, or an analogue or derivative of Vitamin $B_{12}$ possessing binding activity to Castle's intrinsic factor.

According to a second embodiment of this invention there is provided a complex for oral delivery of a substance to the circulation or lymphatic drainage system of a host, comprising:

a microparticle coupled to at least one carrier;

the carrier being capable of enabling the complex to be transported to the circulation or lymphatic drainage system via the mucosal epithelium of the host;

the microparticle being capable of entrapping or encapsulating the substance whereby the substance is substantially unaffected by intestinal digestive substances of the host; and the microparticle being adapted to release the entrapped or encapsulated substance into the circulation or lymphatic drainage system of the host.

In the first and second embodiments each microparticle may have a single carrier coupled to it.

Alternatively, in the first and second embodiments a plurality of carriers which may be the same or different may be coupled to the microparticle.

Alternatively, a plurality of microparticles which may be the same or different and which may contain the same substance or different substances may be coupled to the carrier. Typically, the plurality of carriers is from 2 to 100000, generally from 2 to 10 and typically from 2 to 5. Advantageously, the plurality of microparticles is from 2 to 10 and typically from 2 to 4.

Other molecules may be coupled to the microparticle as long as they do not substantially prevent the carrier from being capable of enabling the complex to be transported to the circulation or lymphatic drainage system via the mucosal epithelium of the host. Such molecules include targetting molecules which target and attach the complex of the first embodiment to or in the vicinity of a desirable target in the host (eg an organ in the host). A carrier molecule which also functions as a targetting molecule may also be used. Examples of targetting molecules include antibodies (including monoclonal and polyclonal antibodies), lectins, enzymes, or other binding proteins or substances (or binding fragments thereof).

According to a third embodiment of this invention there is provided a composition for oral delivery of a substance or substances to the circulation or lymphatic drainage system of a host, comprising a mixture of a plurality of different complexes according to the first embodiment.

The complexes may be different in that the carrier, the microparticle and/or the substance of each complex may be different to the carrier, the microparticle and/or the substance of at least one of the other complexes.

The composition of the third embodiment can also include an acceptable carrier, diluent, excipient and/or adjuvant.

According to a fourth embodiment of this invention there is provided a composition for oral delivery of a substance to the circulation or lymphatic drainage system of a host, comprising the complex of the first embodiment together with a physiologically acceptable carrier, diluent, excipient and/or adjuvant.

According to a fifth embodiment of this invention there is provided a process for preparing a composition for oral delivery of a substance to the circulation or lymphatic drainage system of a host, comprising:

mixing a complex of the first embodiment with at least one different complex of the first embodiment.

The process of the fifth embodiment can further include mixing a physiologically acceptable carrier, diluent, excipient and/or adjuvant with the complex and the least one different complex.

A preferable composition of the fifth embodiment is a medicament comprising a carrier coupled to a microsphere or microcapsule comprising a hormone, drug, immunogen or DNA or RNA (such as ribozyme) component, molecule or analogues thereof in pharmaceutically active form.

According to a sixth embodiment of this invention there is provided a process for preparing a composition for oral delivery of a substance to the circulation or lymphatic drainage system of a host, comprising:

mixing the complex of the first embodiment with a physiologically acceptable carrier, diluent, excipient and/or adjuvant.

The nature of the carrier, diluent, excipient and/or adjuvant utilised in the composition of the third embodiment is dependent on the type of host. For instance, when the host is a human the carrier, diluent, excipient and/or adjuvant is pharmaceutically acceptable. When the host is non human such as an a non human mammal (eg a dog, cat, sheep, goat cow, bull, camel or horse) or other animal, the carrier, diluent, excipient and/or adjuvant is veterinarilly acceptable.

Examples of pharmaceutically acceptable carriers, diluents and excipients for oral delivery include: sodium bicarbonate solutions and similar diluents which neutralise stomach acid or have similar buffering capacity, glycols, oils or emulsions; and include medicaments in the form of gels, pastes and viscous colloidal dispersions. The medicament may be presented in capsule, tablet, slow release or elixir form or as a gel or paste. Furthermore the medicament may be presented as a food.

According to a seventh embodiment of this invention there is provided a method of orally delivering a substance to the circulation or lymphatic drainage system of a host requiring such substance, comprising:

orally administering to the host an effective amount of a complex of the first embodiment or a composition of the third or fourth embodiments.

A preferred method of the seventh embodiment is for treating a vertebrate host by administration of a hormone, drug, immunogen or DNA or RNA (such as ribozyme) component, molecule, analogue or derivative thereof requiring such administration which method comprises the oral administration to the host of an effective amount of a carrier coupled to a microsphere or microcapsule comprising a hormone, drug, immunogen or DNA or RNA (such as ribozyme) component, molecule, analogue or derivative thereof appropriate to the therapy of the host.

According to an eighth embodiment of this invention there is provided a kit for preparing a complex for oral delivery of a substance to the circulation or lymphatic drainage system of a host, comprising:

at least one type of carrier;

at least one type of microparticle;

means to couple the microparticle to the carrier to form the complex;

the carrier being capable of enabling the complex to be transported to the circulation or lymphatic drainage system via the mucosal epithelium of the host;

the microparticle entrapping or encapsulating the substance whereby the substance is substantially unaffected by intestinal digestive substances of the host; and the microparticle being adapted to release the entrapped or encapsulated substance into the circulation or lymphatic drainage system of the host.

The kit may include a plurality of the same or different carriers and/or a plurality of the same or different microparticles. The microparticles may contain the same substance or different substances. The kit may include at least one type of auxiliary molecule such as a targetting molecule and means to couple the auxiliary molecule(s) to the microparticle(s).

Hormones, drugs, immunogens or DNA or RNA (such as ribozyme) component, molecule or analogues thereof suitable to be incorporated within a microparticle, such as a microsphere or microcapsule include all hormones, drugs, immunogens or DNA or RNA (such as ribozyme) component, molecule or analogues thereof for which oral administration is desirable but for which oral administration in an unprotected form results in substantial loss of efficacy.

Thus typical substances for delivery according to the invention include active substances such as hormones and bioactive peptides (and analogues and derivatives thereof) such as LHRH, Vasopressin, oxytocin, Insulin, testosterone, interferon, somatotrophin, somatostatin, Erythropoietin, Colony Stimulating factors (G-CSF, GM-CSF, CSF), PMSG, HcG, Inhibin, PAI-II; therapeutic agents such as neomycin, salbutamol, pyrimethamine, penicillin G, methicillin, cabenicillin, pethidine, xylazine, ketamin HCl, mephensin, GABA, iron dextran, nucleotide analogues or ribozyme.

Further examples of active substances include polypeptides such as insulin, somatostatin, somatostatin derivatives (U.S. Pat. Nos. 4,087,390, 4,093,574, 4,100,117 and 4,253,998), growth hormones, prolactin, adrenocorticotropic hormone (ACTH), melanocyte stimulating hormone (MSH), thyroid hormone releasing hormone (TRH), its salts, and derivatives thereof (U.S. Pat. Nos. 3,957,247 and 4,100,152), thyroid stimulating hormone (TSH), luteinizing hormone (LH), follicle stimulating hormone (FSH), vasopressin, vasopressin derivatives [desmopressin [Folia Endocrinologica Japonica 54, No. 5, p. 676–691 (1978)]]. oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives [U.S. Pat. No. 4,277,394, European patent application Publication No. 31567], endorphin, kyotorphin, interferons (a, b, g), interleukins (I, II, and III), tuftsin, thymopoietin, thymosin, thymostimulin, thymic humoral factor (THF), serum thymic factor (FTS), and its derivatives (U.S. Pat. No. 4,229,438) and other thymic factors [Medicine in Progress 125, No. 10, p. 835–843 (1983)], tumor necrosis factor (TNF), colony stimulating factor (CSF), motilin, dinorphin, bombesin, neurotensin, cerulein, bradykinin, urokinase, asparaginase kallikrein, substance P analogue and antagonist, nerve growth factor, blood coagulation factors VIII and IX, lysozyme chloride, polymixin B, colistin, gramicidin, bacitracin, protein synthesis stimulating peptides (British patent No. 8232082), gastric inhibitory polypeptide (GIP), vasoactive intestinal polypeptide (VIP), platelet-derived growth factor (PDGF), growth hormone releasing factor (GRF, somatocrinin), bone morphogenetic protein (BMP), epidermal growth factor (EGF), etc.

Examples of antitumor agents include bleomycin hydrochloride, methotrexate, actinomycin D, mitomycin C, vinblastine sulfate, vincristine sulfate, daunorubicin hydrochloride, adriamycin, neocarcinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U and poly ICLC.

Examples of antibiotics, include gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam.

The aforementioned antipyretic, analgesic and antiinflammatory drugs include, for instance, sodium salicylate, sulpyrine, sodium flufenamate, sodium diclofenac, sodium indomethacin, morphine hydrochloride, pethidine hydrochloride, levorphanol tartrate and oxymorphone. Examples of the antitussives and expectorants may be mentioned ephedrine hydrochloride, methylephedrine hydrochloride, noscapine hydrochloride, codeine phosphate, dihydrocodeine phosphate, alloclamide hydrochloride, chlophedianol hydrochloride, picoperidamine hydrochloride, cloperastine, protokylol hydrochloride, isoproterenol hydrochloride, salbutamol sulfate and terbutaline sulfate. Examples of sedatives include chlorpromazine hydrochloride, prochlorperazine, trifluoperazine, atropine sulfate and scopolamine methylbromide. The muscle relaxants include, among others, pridinol methanesulfonate, tubocurarine chloride and pancuronium bromide. The antiepileptics include, for instance, sodium phenytoin, ethosuximide, sodium acetazolamide and chlordiazepoxide hydrochloride. Examples of antiulcer drugs include metoclopramide and L-histidine monohydrochloride. Examples of antidepressants include imipramine, clomipramine, noxiptiline and phenelzine sulfate. The antiallergic drugs include, among others, diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride. The cardiotonics include, among others, trans-p-oxocamphor, theophyllol, aminophylline and etilefrine hydrochloride. The antiarrythmic agents include, for instance, propranolol hydrochloride, alprenolol hydrochloride, bufetolol hydrochloride and oxyprenolol hydrochloride. The vasodilators include, among others, oxyfedrine hydrochloride, diltiazem hydrochloride, tolazoline hydrochloride, hexobendine and bamethan sulfate. The antihypertensive diuretics include, among others, hexamethonium bromide, pentolinium, mecamlamine hydrochloride, ecarazine hydrochloride and clonidine hydrochloride. Examples of antidiabetics include sodium glymidine, glypizide, phenformin hydrochloride, buformin hydrochloride and metformin. The anticoagulants include, among others, sodium heparin and sodium citrate. The haemostatic agents include, among others, thromboplastin, thrombin, menadione sodium bisulfite, acetomenaphthone, e-aminocaproic acid, tranexamic acid, carbazochrome sodium sulfonate and adrenochrome monoaminoguanidine methanesulfonate. Among antituberculotics are isoniazid, ethambutol and sodium p-aminosalicylate. The hormone drugs are exemplified by prednisolone succinate, prednisolone sodium phosphate, dexamethasone sodium sulfate, betamethasone sodium phosphate, hexestrol phosphate, hexestrol acetate and methimazole. The antinarcotic agents include, among others, levallorphan tartrate, nalorphine hydrochloride and naloxone hydrochloride.

Suitable carrier molecules include Vitamin $B_{12}$, a Vitamin $B_{12}$ analogue or derivative (as described in PCT/AU86/00299), or a lectin, or "lectin-like" molecule (such as that described in WO086/06635).

Suitable carrier molecules also include bacterial adhesins, viral adhesins, toxin binding subunits and lectins, as well as Vitamin $B_{12}$ and analogues thereof.

Analogues of Vitamin $B_{12}$ for use as carriers for microparticles include cyanocobalamin, aquocobalamin, adenosylcobalamin, methylcobalamin, hydroxycobalamin, cyanocobalamin carbanalide, 5-O-methylbenylcobalamin, and the desdimethyl, monoethylamide and methylamide analogues of all of the preceding analogues, as well as coenzyme $B_{12}$, 5'-deoxyadenosylcobalamin, chlorocobalamin, sulfitocobamin, nitrocobalamin, thiocyanatocobalamin, 5,6-dichlorobenzimadazole, 5-hydroxybenzimidazole, trimethylbenzimidazole, adenosylcyanocobalamin, cobalamin lactone, cobalamin lactam, and analogues in which the cobalt is replaced by zinc or nickel or the corrin ring is replaced by a substituent which does not affect the binding capacity of the analogue to IF.

Derivatives of Vitamin $B_{12}$ for use as carriers for microparticles include the anilide, ethylamide, monocarboxylic and dicarboxylic acid derivatives of Vitamin $B_{12}$ and its analogues as well as tricarboxylic acid or proprionamide derivatives of Vitamin $B_{12}$ or its analogues. They would also include molecules in which alterations or substitutions had been performed to the Corrin ring [viz:-cyano (13-epi) cobalamin Co a-(a 5,6-dimethylbenzimidazoyl)-Co, b-cyano-(13-epi) cobamic a,b,c,d,g, pentaamide, adenosyl-10-chlorocobalamin, dicyanobyrinic heptamethyl ester, cyanoaquacobyrinic acid pentaamide], or where cobalt had been replaced by another metal ion (viz:- nickel, zinc, etc) or various anion or alkyl substituents to the corrin ring such that the binding capacity of the molecule to intrinsic factor is unaffected. The mucosal epithelial cells will take up the intrinsic factor-vitamin $B_{12}$ complex including the microparticle, such as a microsphere or microcapsule attached to the vitamin $B_{12}$ (or suitable analogue) and transepithelially transport the microsphere or microcapsule and deliver them into the circulation where the enclosed substance such as a hormone, drug, immunogen, or DNA or RNA (such as ribozyme) component, molecule or analogues thereof can act.

Derivatives and analogues of vitamin $B_{12}$ are discussed in Schneider, Z. and Stroinski, A.; *Comprehensive* $B_{12}$; Walter De Gruyter; Berlin, NY: 1987, the disclosure of which is incorporated herein by reference.

Similarly, if a microparticle, such as a microsphere or microcapsule is administered orally and complexed to a carrier protein possessing binding activity to the mucosal epithelium, the cells of the mucosal epithelium take up those molecules including the microparticles, such as microspheres or microcapsules attached to the carrier proteins and present the microsphere or microcapsule to the circulation where the substance such as a drug, hormone, immunogen or DNA or RNA (such as ribozyme) component, molecule or analogues thereof enclosed therein can act.

Polymers suitable for the formation of microspheres by solvent evaporation (in liquid drying) include, amongst others, Poly-lactic acid, Poly-(Lactide/co-glycolide), Poly-hydroxybutyrate, Poly-hydroxyvalerate, Poly-(hydroxybutyrate/valerate), Ethyl cellulose, Dextran, Polysaccharides, Polyalkylcyanoacrylate, Poly-methylmethacrylate, poly(e-caprolactone) and various combinations and co-polymers of the above.

Polymers suitable for the formation of microspheres by interfacial precipitation/polymerization include, amongst others, EUDRAGIT™; Poly($N^a, N^e$-L-lysinediylterephthaloyl); polymers formed by the reaction of Lysine hydrochloride and p-phthaloyl dichloride; by the reaction of acryloylated maltodextrin or acryloylated hydroxyethyl starch with ammonium peroxodisulfate and N,N,N',N'-tetramethylethylenediamine. Microspheres can also be formed by the polymerization of various diamines such as ethylene diamine, phenylenediamine, toluene diamine, hexamethylene diamine, or diols such as ethylene diol, bisphenol, resorcinol, catechol, pentanediol, hexanediol, dodecanediol, 1,4 butanediol, with diacid chlorides such as sebacoyl chloride and adipoyl chloride, or diisocyanates such as hexamethylene diisocyanate using the methods fully described in EP-A-85870002.4, the disclosure of which is incorporated herein by reference.

Polymers suitable for the formation of microspheres by polymer phase separation include co-poly(vinyl chloride:vinyl alcohol:vinyl acetate), cellulosic polymers, polyvinyl acetate, polyvinyl alcohol, polyvinylchloride, natural and synthetic rubbers, polyacrylates, polystyrene and the like. Methods and materials to synthesize such microspheres are fully described in U.S. Pat. No. 4,166,800, the disclosure of which is incorporated herein by reference.

Polymers suitable for the formation of microspheres by complex coacervation include, amongst others, mixtures of polyanions, such as gum arabic, alginate, carboxymethyl cellulose, carboxymethyl starch, polystyrene sulfonic acid, polyvinyl sulfonic acid, poly-glucuronic acid, Poly-pyruvic acid, carrageenan, heparin sulphate, polyphosphate with polycations, such as polylysine, gelatin.

Polymers suitable for the formation of microspheres by Polymer/Polymer incomoatability include, amongst others, ethyl cellulose, Ethylene vinyl acetate polymer, Poly (lactide), or Poly(vinylidene chloride) mixed with polymers such as Polyethylene, Silicone, Polyisobutylene or Polybutadiene.

Other materials suitable for formation of microspheres include, Starch, Cross-linked Albumen, Polyacrylamide, Cross-linked gelatin and others obvious to those skilled in the art of microsphere preparation. Materials suitable for the formation of microspheres, and methods for the preparation of microspheres, are described in U.S. Pat. Nos. 3,936,573 and 3,962,414, the disclosures of which are incorporated herein by reference.

According to the present invention there is also provided a process for the production of a complex of the invention, which process comprises one or more of the following steps:

(a) reacting microparticles with a carrier molecule to form the complex;

(b) chemically modifying a carrier molecule to provide at least one functional group capable of forming a chemical linkage and reacting a microparticle and the modified carrier molecule to form the complex;

(c) reacting microparticles with at least one cross-linking agent and reacting the reacted microparticles with a carrier molecule to form the complex;

(d) reacting a carrier molecule with at least one cross-linking agent and reacting microparticles with the reacted carrier molecule to form the complex;

(e) reacting microparticles and a carrier with at least one cross-linking agent to form the complex;

(f) reacting microparticles with at least one cross-linking agent, reacting a carrier molecule with at least one cross-linking agent and reacting the reacted microparticles and the reacted carrier molecule to form the complex; or (g) reacting a carrier molecule with a hydrophobic moiety and reacting microparticles with the reacted carrier molecule to form a complex non-covalently bonded by hydrophobic interaction.

As an example of reaction (g) above, in order to link Vitamin $B_{12}$ to the surface of microparticles which have no readily available chemical groups suitable for chemical conjugation, it is possible to prepare a complex of Vitamin $B_{12}$ to an hydrophobic moiety which can insert, non-covalently, into the surface of the microparticles. Such a molecule is easily added at the time of formation of the microparticles. The strength of the hydrophobic association is such that there is only a very slow dissociation of the Vitamin $B_{12}$ from the microparticles under physiological conditions. Similarly, other carrier molecules may be reacted with hydrophobic moieties, for formation of an hydrophobically-associated complex with a microparticle.

Suitable hydrophobic moieties which can be used for reacting with a carrier molecule are aliphatic or aromatic chains or amphipathics containing a water soluble head and a lipid soluble tail suitable for hydrophobic association within an hydrophobic environment. Examples include oleic acid, octanoic acid, linoleic acid, stearic acid, palmitic acid or glycerophosphoric acids, which may be directly conjugated to an amino group of a carrier molecule using a suitable carbodiimide (for example dicyclohexylcarbodiimide (DCC), or 1-ethyl-3-(3-dimethylaminopropylcarbodiimide (EDAC)). Similarly, any amphiphathic molecule possessing an amino-group , for example amino-hexane, amino-decane, amino-dodecane, amino-tetradecane, amino-hexadecane or phosphatidylethanolamine, may be conjugated directly to carboxyl groups using carbodiimides.

Alternatively, the carrier molecule may be linked covalently, directly or indirectly to the microparticle. Where a cross-linking agent is used, the cross-linking agent may contain a disulfide bond or be cleavable by acid, base or periodate. Examples of cross-linking agents include: N-(4-azidophenylthio)-phthalimide; 4,4'-dithiobisphenylazide; dithio-bis-(succinimidyl-propionate); dimethyl-3,3'-dithiobis-propionimidate.2HCl; 3,3'-dithio-bis-(sulfosuccinimidyl-propionate); ethyl-(4-azidophenyl)-1,3'-dithiopropionate; sulfo-succinimidyl-2-(m-azido-o-nitrobenzamido)-ethyl-1,3'-dithiobutyrimidate.HCl; N-succinimidyl-(4-azido-phenyl)-1,3'dithiopropionate; sulfo-succinimidyl-2-(m-azido-o-nitro-benzamido)-ethyl-1,3'-dithiopropionate; sulfo-succinimidyl-2-(p-azido-salicylamido)-ethyl-1,3'-dithiopropionate; N-succinimidyl-3-(2-pyridylthio)propionate; sulfosuccinimidyl-(4azidophenyidithio)-propionate; 2-iminothiolane; disuccinimidyl tartrate; bis-[2-(succinimidyloxycarbony-ethyl]-sulfone and carbodiimides. A description of suitable carbodiimides is provided in Khorana, H. G. (1953) Chem. Rev. 53: 145–166, the disclosure of which is incorporated herein by reference.

Examples of suitable methods of reacting vitamin $B_{12}$ ($VB_{12}$) derivatives with functionalised microparticles include:

(i). Reaction of carboxy-$VB_{12}$ with amine $$VB_{12}\text{–}COOH + NH_2\text{–}R \xrightarrow{\text{EDAC}} VB_{12}\text{–}CONH\text{–}R + H_2O$$

(ii). Reaction of carboxy-$VB_{12}$ with phenol $$VB_{12}\text{–}COOH + HO\text{–}Ph\text{–}R \xrightarrow{\text{EDAC}} VB_{12}\text{–}CO\text{–}O\text{–}PH\text{–}R + H_2O$$

(iii) Reaction of amino-VB12 with carboxylates $$VB_{12}\text{–}NH_2 + COOH\text{–}R \xrightarrow{\text{EDAC}} VB_{12}\text{–}NHCO\text{–}R + H_2O$$

Methods of coupling vitamin $B_{12}$ derivatives to various functional groups are also described in U.S. Pat. No. 4,465,775, United Kingdom Patent No. 1,345,327 and U.S. Pat. No. 3,981,863, the disclosures of which are incorporated herein by reference.

Suitable cross-linking of the carrier and the microspheres may be achieved by acid hydrolysis of the amide side groups of the propionamide side chains adjacent to rings A, B, C or D of Vitamin $B_{12}$ and coupling to suitable side groups of the microspheres.

The carrier molecule or cross-linking agent may react with a functional group or a modified functional group present on, or introduced onto the surface of the microparticle. Suitable functional groups for reaction with the carrier molecule or cross-linking agent include carboxyl, hydroxyl, amino, thio, amido, hydrazo, azido, phenolic, ester, aldehyde, ketone, sulfate, halo, phosphate, isocyanato and isothiocyanato groups. Suitable reagents for modification or introduction of functional groups include hydrazine, periodate, permanganate or other oxidising agents, borohydrides, metallic hydrides or other reducing agents.

Alternatively, a spacer molecule may be used to link the carrier molecule to the microparticle. Examples of such spacer molecules include bifunctional molecules such as diamines, dicarboxylic acids, diols, aminocarboxylic acids, dithiols, diesters, diphenols, and other like molecules.

Advantageously, using a complex of the present invention, a substance such as a hormone, drug or immunogen can be presented via the mucosal epithelium of a host, in a pharmaceutically active form to the circulation or lymphatic drainage system of a host. Initially, microparticles such as microspheres or microcapsules, containing a substance such as a pharmaceutically active agent, are prepared and linked, generally covalently, to a suitable carrier (generally a mucosal binding protein or Vitamin $B_{12}$ or an analogue or derivative thereof) such that the carrier maintains its ability to interact with the intestinal mucosa or intrinsic factor (respectively). Then the microparticles are administered orally to a host and as a result of this administration the carrier-microparticles and the substance contained therein pass into the circulation or lymphatic drainage system of the host. In this fashion the substance is protected from the degradative contents of the intestinal milieu, and the uptake capacity of the carrier is amplified.

Thus, a complex according to the first embodiment of the present invention overcomes the disadvantages inherent in the mucosal binding protein and Vitamin $B_{12}$ uptake system, viz:- the need for substances, such as pharmaceutical agents, to be resistant to gastro-intestinal enzymes and pH conditions, as well as the limited uptake capacity of the uptake systems.

The present invention relies on the ability to entrap substances, which are generally small molecules, such as hormones, proteins, peptides, drugs, etc, within a matrix or capsule, generally fabricated from a suitable polymer, in such a way as to form very small microparticles such as microcapsules or microspheres. Once trapped within these microparticles it is possible using suitable chemistry to link, generally covalently link, these microparticles to a suitable carrier.

A system for oral delivery of an active substance coupled directly to Vitamin $B_{12}$ is limited in the amount of active substance that can be delivered by the uptake capacity of the IF-dependent uptake mechanism. In humans, this mechanism can only deliver 1–2 µg doses of vitamin $B_{12}$ per feeding (see Cobaiamin. Biochemistry and Pathophysiology. Ed Babior, B. M., Wiley-interscience, NY, 1975.) Similarly, when microencapsulated active agents are administered orally, typically only from 0.1% to 1% of the active agent administered is delivered into the bloodstream (Gruber, R. Longer, M. A. and Robinson, K. J. R. 1987: Some Biological Issues in Oral Controlled Drug Delivery, Adv. Drug Delivery Rev. 1: 1–18).

Using carrier-microparticle complexes of the present invention, however, there is the potential to amplify the uptake of a substance administered orally, some 10 one million times (depending upon the size of microparticle and the loading) as well as to protect the entrapped substance, typically a pharmaceutical agent, from intestinal digestive substances of the host, typically, gastrointestinal enzymes. By choosing a suitable substance for the microparticle such as a bio-degradable polymer the entrapped substance is released once the carrier mediated uptake system has delivered the carrier-microsphere complex to the circulation.

Amplification of Vitamin $B_{12}$ uptake capacity by the incorporation of pharmaceutical active agents into microspheres is illustrated in the following Table 1.

TABLE 1

Amplification of the Vitamin $B_{12}$ uptake capacity by the incorporation of pharmaceutically active agents into microspheres. Total delivery to man.

| Microsphere diameter (nm) | Volume (cc) | Weight of microspheres[1] | Weight of pharmaceutical[2] | Quantity delivered[3] |
|---|---|---|---|---|
| — | — | — | 1 nm | 0.001–0.01 nm |
| — | — | — | 1 nm + $VB_{12}$ | 0.1–1 nm |
| 20 | $4 \times 10^{-18}$ | 2.4 mg | 240 µg | 0.24–2.4 µg |
| 20 | $4 \times 10^{-18}$ | 2.4 mg | 240 µg + $VB_{12}$ | 0.24–240 µg |
| 200 | $4 \times 10^{-15}$ | 2.4 gm | 240 mg | 0.24–2.4 mg |
| 200 | $4 \times 10^{-15}$ | 2.4 gm | 240 mg + $VB_{12}$ | 0.24–240 mg |
| 2000 | $4 \times 10^{-12}$ | 2.4 kg | 240 gm | 0.24–2.4 gm |
| 2000 | $4 \times 10^{-12}$ | 2.4 kg | 240 gm + $VB_{12}$ | 0.24–240 gm |

[1]Data is calculated from the uptake capacity for Vitamin $B_{12}$ of 1 nanomole per feed in man, which represents $6 \times 10^{14}$ molecules of Vitamin $B_{12}$.
[2]Each microsphere would be loaded to a 10% drug loading.
[3]With normal unassisted uptake approximately 0.1–1% of the dose of an orally administered pharmaceutical will cross the intestinal wall and enter the circulation. The Vitamin $B_{12}$ uptake mechanism has the capacity to amplify this uptake by at least one hundred fold.

A particular advantage of the carrier-microparticle complexes of the present invention compared with the carrier-active agent complexes of the prior art is that, there is no chemical modification of the active substance in the complexes of the present invention.

BEST MODE AND OTHER MODES FOR CARRYING OUT THE INVENTION

Microspheres containing a substance such as a hormone, drug, immunogen, or DNA or RNA (such as ribozyme) component, molecule or analogues thereof, are prepared typically by one or more of a number of techniques commonly known to those knowledgeable in the art, including: Solvent evaporation, Complex coacervation, Polymer/polymer incompatibility, Gelation, Interfacial polymerization and Thermal denaturation.

For oral delivery microspheres are complexed with a carrier molecule by direct reaction or by use of cross-linking agents to provide a complex in which the carrier molecule is still able to undergo the binding reactions required for the uptake and transport of the complex and the pharmacological activity of the entrapped active substance is maintained. The carrier molecule is a mucosal binding protein or Vitamin $B_{12}$, or an analogue or derivative of Vitamin $B_{12}$ possessing binding activity to Castle's intrinsic factor.

A medicament containing an effective amount of the complex is formulated by mixing the complex with a pharmaceutically acceptable carrier, diluent, excipient and/or adjuvant. The medicament is prepared so as to be suitable for administration to a patient requiring treatment such as one or more of the conditions outlined in the body of the specification. The medicament is prepared using standard pharmaceutical techniques.

It is recognised that a number of factors will affect the determination of an appropriate dosage for a particular patient. Such factors include the age, weight, sex, general health and concurrent disease states of the patient. The determination of the appropriate dose level for the particular patient is performed by standard pharmaceutical techniques.

The medicament is orally administered to the patient in an amount such that an appropriate effective dosage of the substance in the complex contained in the medicament is delivered to the circulation or lymphatic drainage system of the patient.

The invention is further described with reference to the following examples which are in no way limiting on the scope of the invention.

Throughout the following examples, reference to "$VB_{12}$" is to be taken as reference to Vitamin $B_{12}$.

EXAMPLE 1

Preparation of Microspheres by Coacervation

Almost any protein can be used as the matrix for entrapping drug via the desolvation technique, however preferred proteins according to the invention include bovine serum albumen (BSA), Ovalbumen (OA), collagen, Microspheres were prepared by coacervation of BSA following desolvation, according to the method of Oppenheim (Oppenheim, 1984, Oppenheim et al 1984, 1982), Briefly a 40% ammonium sulphate solution was added dropwise to a solution of 1% BSA containing 0.5% Tween 20 and the turbidity monitored by Klett readings, until the turbidity rose rapidly. At this point (determined by experimentation) the solution was placed in an ultra-turrax and 600 ul of glutaraldehyde added to cross-link the nanoparticles. Cross-linking was stopped by the addition of a solution of 12% sodium metabisulfite.

Particles were then washed extensively with distilled water prior to coupling to the amino-derivative of Vitamin $B_{12}$.

EXAMPLE 2

Incorporation of Neomycin Sulphate

For incorporation of the antibiotic, neomycin sulphate, neomycin sulphate was dissolved at 10 g/100 ml of the BSA/Tween solution. Desolvation and cross-linking was carried out as described in Example 1.

EXAMPLE

Preparation of Insulin Microspheres

Insulin microspheres were prepared in a similar fashion to the BSA microspheres except the initial desolvation was achieved by the dropwise addition of 0.1 N HCl, while resolvation was achieved by the addition of 0.1 N NaOH.

EXAMPLE 4
Coupling of Microspheres to Amino-ethyl-Vitamin $B_{12}$

The monocarboxylic acid derivative of Vitamin $B_{12}$ was prepared as previously described by Allen and Majerus (1972). The diamino-ethane derivative of COOH-Vitamin $B_{12}$ was prepared by reacting N,N-dicyclohexyl carbodiimide with a solution of diaminoethane (pH 6.5). The amidated derivative was purified by HPLC.

Proteinaceous microspheres were coupled to amino-ethyl Vitamin $B_{12}$ by reaction with N,N-dicyclohexyl carbodiimide.

EXAMPLE 5
Oral Feeding

The $VB_{12}$-microsphere complex can be administered orally by feeding in a solution of 0.1 M carbonate buffer pH 9.5.

Uptake of the $VB_{12}$-microspheres occurs via the intrinsic factor mediated $VB_{12}$ uptake mechanism.

EXAMPLE 6
Preparation of $VB_{12}$-Lipid Complexes for Hydrophobic insertion into Microspheres a) Preparation of $VB_{12}$-phosphatidyl ethanolamine ($VB_{12}$-PEA)

Phosphatidylethanolamine (PEA, 100 mg) was dissolved in 2 ml chloroform/methanol (50:50, v/v). Monocarboxyl $VB_{12}$ ("e" isomer) (100 mg) was added to the mixture. The monocarboxylic acid isomer was then cross-linked to the PEA by the addition of 200 mg of the carbodiimide, 1-ethyl-3-(3-dimethylaminopropyl)carbodiimide (EDC or EDAC). The reaction was allowed to proceed for 90 minutes prior to the addition of the $VB_{12}$-PEA to microspheres.

b) Preparation of other complexes between $VB_{12}$ and an hydrophobic moiety

Covalent complexes can be made between analogues of $VB_{12}$ and almost any aliphatic or aromatic chains or amphipathic molecule containing a water soluble head group suitable for conjugation and a lipid soluble tail suitable for hydrophobic association within an hydrophobic environment. Thus, any lipid (saturated, unsaturated or polyunsaturated) which has a carboxylic acid head group, such as Oleic acid, octanoic acid, linoleic acid or glycerophosphoric acids may be directly conjugated to an amino-$VB_{12}$ derivative using a suitable carbodiimide (EDAC or dicyclohexylcarbodiimide, for example). Similarly any amphiphathic molecule possessing an amino-group (amino-hexane, amino-decane, amino-dodecane, phosphatidyl-ethanolamine) may be conjugated directly to carboxy-$VB_{12}$ using carbodiimides.

EXAMPLE 7
Preparation of $VB_{12}$-Microspheres by Solvent Evaporation a) Preparation of $VB_{12}$-PEA-[Polymethylmethacrylate] microspheres Polymethylmethacrylate (PMM, Polysciences)(MW 12,000; 500 mg) was dissolved in 2 ml of dichloromethane (DCM). The PMM in DCM was then added dropwise to 20 ml of 0.25% Polyvinylalcohol (PVA) while homogenizing at 13,500 rpm with a Janke & Kunkel Ultraturrax. After 1 minute, 200 µl of $VB_{12}$-PEA was added and stirred gently overnight. The pink microspheres were then harvested by centrifugation, washed three times with water and lyophilized.

b) Preparation of $VB_{12}$-[PEA-Poly-lactic acid] microspheres

Poly-lactic acid (PLA, Polysciences)(MW 50,000; 500 mg) was dissolved in 3 ml of DCM and then homogenized into 20 1% PVA at 13,500 rpm on an Ultraturrax T25 with an S25F probe for 5 minutes. $VB_{12}$-PEA (400 µl) was added while the solution was stirred gently. Microspheres were harvested as described above.

c) Preparation of $VB_{12}$-[PEA-Poly-Hydroxy-butyrate/valerate] microspheres Poly-Hydroxy-butyrate/valerate (9% valerate) (ICI; 500 mg) was dissolved in 5 ml of DCM and homogenized into 20 ml 1% PVA at 13,500 rpm on an Ultraturrax T25 with an S25F probe for 5 minutes. $VB_{12}$-PEA (400 µl) was added and the spheres processed as described in 8b.

EXAMPLE 8
Covalent conjugation of $VB_{12}$ to Microspheres with Surface Carboxyl groups A general method for the conjugation of $VB_{12}$ to the surface of microspheres made from polymers with free carboxyl groups is outlined below. The specific example utilizes commercially available carboxyl-modified microspheres. Polysciences Fluoresbrite™ carboxylate Microspheres (2.5% Solids Latex) were obtained from Polysciences in sizes of 0.045 um, 0.49 um, 2.2 um and 9.97 um. One ml of each of the preparations was washed extensively with distilled (DW) and resuspended in 200 µl of distilled water. To each preparation was added 1.5 mg aminododecyl $VB_{12}$ then 5 mg of EDAC. Each preparation was allowed to react overnight, after which unreacted material was removed by repeated washing with DW or by dialysis against DW.

EXAMPLE 9
Surface Derivatization of Microspheres

Many polymers used in the preparation of microspheres by solvent evaporation do not contain functional groups for direct conjugation to $VB_{12}$ or its functionalized analogues, however it is possible to modify the surface of the preformed microspheres to introduce functional groups suitable for conjugation to $VB_{12}$.

a) Surface derivatization of Polylactic acid (PLA) microspheres

A preformed PLA microspheres (10 mg) were gently suspended in DW (350 µl) by rotation on a rotary shaker for 2 hours. Hydrazine hydrate (10 µl) was added and the suspension was shaken overnight at room temperature. The spheres were spun down and repeatedly washed with water by re-suspension and centrifugation. The washing procedure was repeated until the supernatant failed to give a positive hydrazine test (purple colour upon reaction with a solution of trinitrobenzenesulfonate; 1 mg /ml). The spheres were washed a further two times and the wet pellet used directly for conjugation to $VB_{12}$.

b) Conjugation of $VB_{12}$ to hydrazine modified PLA microspheres

A sample of the hydrazine modified PLA microspheres (3 µl wet pellet) was suspended in DW (250 µl). Aqueous solutions of the "e" monocarboxylic acid isomer of $VB_{12}$ ("e"$CB_{12}$)(10 mg/ml, 400 µl) and EDAC (100 mg/ml, 100 µl) were added and the reaction mixture shaken overnight at room temperature. The suspension was spun down and the supernatant removed. The pellet was washed repeatedly with DW (6 washes). The residual pellet, which was pale pink in colour, was vacuum dried prior to measurement in the IF assay.

Two control reactions were performed concurrently with the above conjugation. In the first a 3 mg sample of hydrazine-modified PLA microspheres was treated with the "e"$CB_{12}$ as described above but DW was used in place of the EDAC solution. In the second control a 2 mg sample of unmodified PLA microspheres was treated with both "e"$CB_{12}$ and EDAC as described above. For both controls the pellet remaining after repeated washing was a clear white colour with no evidence of any associated $VB_{12}$.

EXAMPLE 10
Intrinsic Factor Binding Assay

The ability of various $VB_{12}$-microsphere preparations to bind to porcine intrinsic factor was assessed in an intrinsic factor binding assay.

$VB_{12}$ and $VB_{12}$-microsphere preparations were diluted out in six-tenfold dilutions in IF buffer (1 mg/ml BSA [$B_{12}$ and IF deficient; Sigma #A-3902] in 0.1 M Phosphate buffer pH7.5). To 225 µl of IF buffer was added 25 µl of the above dilutions. $Co^{57}VB_{12}$ (0.25 ml, 0.25 ng in IF buffer) was then added to each sample. Porcine IF (0.25 ml; 1 IU/ml in IF buffer) was then added and the material allowed to incubate at RT for 20 min. BSA-coated charcoal (0.25 ml; 0.5% BSA ($B_{12}$ and IF free) plus 2.5% charcoal) was added to each sample, vortexed and then centrifuged. The supernatant from each sample was then counted on a gamma counter set for counting $Co^{57}$. Results were determined as a percentage inhibition of the $Co^{57}$-$VB_{12}$ binding.

EXAMPLE 11
Estimation of IF Binding Activity of $VB_{12}$ Microspheres

Microspheres prepared with $VB_{12}$ surface coating were examined for IF binding as described above. The percentage binding is presented in the table below.

TABLE 2

IF binding of various $VB_{12}$-microsphere preparations.

2a. IF binding by VB-Carboxylate microspheres (See Example 8)

| Microsphere preparation | MS weight | % inhibition of binding[1] |
|---|---|---|
| Carboxylate 9.97 µm | 0.625 mg | 27% |
| Carboxylate 1.87 µm | 62.5 µg | 62% |
| Carboxylate 0.49 µm | 6.25 µg | 40% |
| Carboxylate 0.045 µm | 0.625 µg | 90% |

2b. IF binding by $VB_{12}$-PEA coated microspheres

| Microsphere preparation | Microsphere weight[2] |
|---|---|
| $VB_{12}$-PEA-PMM microspheres[3] | 140 µg |
| $VB_{12}$-PEA-PLA microspheres[3] | 100 µg |
| $VB_{12}$-PEA-PHB/PHV microspheres[3] | 75 µg |
| "e"$VB_{12}$-hydrazide-PLA microspheres[4] | 100 µg |

[1]Data is presented as the percentage inhibition of binding of $Co^{57}B_{12}$ to 2 U IF.
[2]Data is expressed as the weight of microspheres which could showed equivalent IF binding as 10 ng of $VB_{12}$.
[3]Microspheres prepared as in Example 8.
[4]Microspheres prepared as in Example 9.

EXAMPLE 12
Covalent Conjugation of Mucosal Immunogens to Fluorescent Microspheres Amino-ethyl derivatized Polysciences Fluoresbrite™ carboxylate Microspheres (2.5% Solids Latex) in sizes of 0.045 µm, 0.49 µm, 2.2 µm and 9.97 µm were prepared by the addition of 500 µl of 0.1 M diaminoethane pH 6.5 to 2 ml of spheres suspended to 2.5%. Surface modification was then obtained by the addition of 50 mg of dry EDAC to each preparation. Unreacted material was removed by centrifugation and washing with DW. Finally microspheres were resuspended in 3 ml of DW. The spheres were then separated into 3×1 ml aliquots and treated as follows:

a) Conjugation to LTB

Amino-ethyl microspheres were activated with glutaraldehyde by the addition of 40 µl of a 25% solution of glutaraldehyde plus 100 µl of 0.1 M sodium phosphate buffer pH 6.5.After reaction for 20 minutes at room temperature, 100 µl of 1 M HCL was added to the spheres which were then washed twice by centrifugation and resuspension in 10 mM HCl. Finally the spheres were resuspended in 1 ml of DW. LTB (2 mg in 1 ml 0.1 M carbonate buffer pH 9.5) was then added and allowed to conjugate to the activated microspheres overnight. Finally the Schiff's base formed during the conjugation was stabilized by reduction with 200 µl of cold sodium borohydride for two hours on ice. The microspheres were then washed 3 times in 0.1 M carbonate buffer, pH 9.5, and resuspended in 500 µl of the same buffer. Microspheres were then stored at 4° C. until used for oral feeding.

b) Conjugation to K99 pili

Glutaraldehyde activated amino-ethyl microspheres (prepared as described in Example 13a) were conjugated to K99 pili by the addition of 2 ml of K99 pili (1 mg/ml) plus 100 µl of 0.1 M carbonate buffer and reaction overnight at room temperature. The Schiff's base was reduced and the microspheres washed as described in Example 12a.

c) Conjugation to 987P pili Amino-ethyl microspheres (1 ml) were conjugated to 987P pili (2 mg in 200 µDW) by the addition of 20 mg of EDAC. After reaction overnight the spheres were washed with 0.1 M carbonate buffer, pH 9.5, as described previously.

Example 13
Oral Administration of Fluoresbrite Microspheres Conjugated to $VB_{12}$, 987P, K99 and LTB Fluoresbrite Microspheres conjugated to $VB_{12}$, 987P, K99 and LTB were orally administered to conscious mice using a suitable feeding needle. At various times after oral administration the mice were killed by cervical dislocation and the small intestines removed surgically. The intestinal contents were then removed by washing the intestines with a solution containing 0.1% Tween 20 in 0.1 M phosphate buffer pH 7.4. The small intestine was then cut into four sections, filled with embedding media and frozen prior to sectioning in a cryostat. Sections were examined by light microscopy using a ZEISS fluorescent microscope.

Close examination of sections obtained from mice fed microspheres conjugated to either $VB_{12}$, 987P, K99 or LTB revealed very similar patterns of binding of spheres to the tips of intestinal epithelial cells. Microspheres of sizes 0.047 µm, 0.45 µm and 1.87 µm could be seen clearly adhering to the tips of the epithelial cells within 2 hours of feeding, regardless of which molecule the microspheres were coated with. The pattern of binding varied somewhat depending upon the coating of the microspheres, thus $VB_{12}$ coated microspheres were found to bind mainly to the cells of the ileum and lower jejunum, while microspheres coated with LTB were found to bind down the entire length of the small intestine. Microspheres coated with either 987P pili or K99 pili were found to bind most predominantly in the jejunum. In some sections, microspheres of up to 0.45 µm appeared to have entered the body of the epithelial cell.

Example 14
Oral Administration of PLA Microspheres Containing $I^{125}$-BSA and Coated with $VB_{12}$-PEA Two preparations of PLA microspheres were synthesized as described previously. Prior to synthesis $I^{125}$-BSA was added to the PLA in DCM. $VB_{12}$-PEA was added to one of the preparations during the solvent evaporation step. Solvent was evaporated overnight, after which the microspheres were washed extensively with distilled water. Microspheres suspended in 0.1% BSA in saline were then fed to female Swiss mice. At various times after feeding, the mice were bled from the retro-orbital plexus and $I^{125}$ counts determined in a Beckman gamma counter.

TABLE 3

Uptake of $I^{125}$ BSA incorporated into PLA spheres or PLA spheres coated with $VB_{12}$-PEA

| Microsphere preparation | Counts in the blood* | | |
|---|---|---|---|
| | T60 | T150 | T240 |
| PLA | 0.76 ± 0.19 | 0.56 ± 0.02 | 0.51 ± 0.02 |
| PLA + $VB_{12}$-PEA | 1.61 ± 0.14 | 1.15 ± 0.01 | 1.29 ± 0.02 |
| p-value | <0.01 | <0.01 | <0.01 |

*Counts are represented as the percentage of counts released from the stomach of mice fed the various microsphere preparations. The data are presented as the average of three mice ± 1 standard deviation.

As can be seen from the data, there was a highly signficant increase in the amount of BSA which was taken up into the blood in mice fed $VB_{12}$-PEA microspheres in comparison to those fed the PLA spheres alone.

INDUSTRIAL APPLICABILITY

The present invention provides a simple and novel technique for the specific protection of active substances comprised within a complex during their transit down the intestine, prior to Intrinsic Factor or mucosal binding protein mediated uptake of the complexes. The invention also provides a method for the amplification of the $VB_{12}$ uptake system. Thus the present invention provides a simple and novel technique for the specific protection of active substances from enzymatic degradation as well as for amplification of the $VB_{12}$ uptake system thus enabling a wide range of active agents to be actively absorbed intact from the intestine.

REFERENCES

Oppenheim R. C. (1984) in "Polymeric Microparticles" (Guiot, P and Couvreur, P. Eds.) CRC Press, Boca Raton. Oppenheim R. C., Gipps, E. M. Forbes, J. F. and Whitehead R. H. (1984) in "Microspheres and Drug Therapy" (Davis, S. S., Illum, L., McVie, J. G. and Tomlinson, E. Eds) Elsevier Science Publishers B. V. Oppenheim, R. C., Stewart, N. F., Gordon, L. and Patel, H. M. (1982) Drug Devel. Indust. Pharm. 8: 531–546. Allen, R. H. and Majerus, P. W. (1972) J.Biol. Chem. 247: 7702–7717.

What is claimed is:

1. A complex for oral delivery of a substance to the circulation or lymphatic drainage system of a host, comprising the substance, a microparticle and a carrier, wherein:

said substance is entrapped or encapsulated in said microparticle and therein is not deleteriously affected by intestinal digestive substances following oral administration of said complex to the host;

said microparticle is a microsphere or microcapsule having a diameter of 1 nanometer to 150 micrometers and is coupled to said carrier by covalent bond, hydrophobic interaction or both;

said carrier is Vitamin $B_{12}$ or a Vitamin $B_{12}$-analogue that binds Castle's intrinsic factor and said carrier is effective to transport said complex via the intestinal mucosal epithelium into the circulation or lymphatic drainage system of the host, and said substance is released from said microparticle into the circulation or lymph after said complex is transported via the intestinal mucosal epithelium into the circulation or lymphatic drainage system of the host.

2. A complex for oral delivery of a substance to the circulation or lymphatic drainage system of a host, comprising the substance, a microparticle and a carrier, wherein:

said substance can be entrapped or encapsulated in said microparticle and therein is not deleteriously affected by intestinal digestive substances following oral administration of said complex to the host;

said microparticle is a microsphere or microcapsule having a diameter of 1 nanometer to 150 micrometers and is coupled to said carrier by covalent bond, hydrophobic interaction or both;

said carrier is Vitamin $B_{12}$ or a Vitamin $B_{12}$-analogue that binds Castle's intrinsic factor and said carrier can transport said complex via the intestinal mucosal epithelium into the circulation or lymphatic drainage system of the host, and said microparticle can release said substance into the circulation or lymph after said complex is transported via the intestinal mucosal epithelium into the circulation or lymphatic drainage system of the host.

3. A process for the production of a complex of claim 1, from a microparticle microsphere or microcapsule having a diameter of 1 nanometer to 150 micrometers and a carrier Vitamin $B_{12}$ or a Vitamin $B_{12}$-analogue that binds Castle's intrinsic factor, said process comprising one or more of the steps of:

(a) reacting said microparticles with said carrier molecule to form said complex;

(b) chemically modifying said carrier to form at least one functional group capable of forming a chemical linkage with said microparticle and then reacting the chemically modified carrier to form the complex;

(c) reacting said microparticle with at least one cross-linking agent and then with a carrier thereby linking said microparticle and carrier together in a complex;

(d) reacting said carrier with at least one cross-linking agent and then with said microparticle thereby linking said carrier molecule and said microparticle together in a complex;

(e) reacting said microparticle and said carrier with at least one cross-linking agent to form said complex;

(f) reacting said microparticle with at least one cross-linking agent, reacting said carrier with at least one cross-linking agent, and then reacting the products of said reactions to form said complex; or (g) reacting said carrier with a hydrophobic moiety and then reacting the product of this reaction with said microparticle to form a complex in which the carrier and microparticle are bonded together non-covalently by hydrophobic interaction.

4. A kit for preparing a complex for oral delivery of a substance to the circulation or lymphatic drainage system of a host, comprising:

(A) at least one microparticle microsphere or microcapsule having a diameter of 1 nanometer to 150 micrometers;

(B) a substance entrapped or encapsulated in said microparticle whereby said substance is not deleteriously affected by intestinal digestive substances when said complex is administered orally to a host and said substance is released from said microparticle into the circulation or lymph when said complex enters the circulation or lymphatic drainage system of the host;

(C) at least one carrier Vitamin $B_{12}$ or a Vitamin $B_{12}$-analogue molecule that binds Castle's intrinsic factor and is effective to transport a complex via the intestinal mucosal epithelium into the circulation or lymphatic drainage system of the host;

(D) one or more reagents to couple said microparticle to said carrier by covalent bond, hydrophobic interaction or both to form a complex, wherein said reagents can couple said microparticle to said carrier to form a complex which, upon oral administration, is transported via the intestinal mucosal epithelium into the circulation or lymphatic drainage system and releases said substance into the circulation or lymph of said host.

5. A complex according to claim 1, wherein the microsphere or microcapsule entraps or encapsulates a hormone, drug, immunogen, ribozyme, DNA or RNA.

6. A complex according to claim 2, wherein the microsphere or microcapsule is capable of entrapping or encapsulating a compound selected from the group consisting of a hormone, drug, immunogen, DNA or RNA.

7. A complex according to claim 1, wherein the covalent bonding is by a cross-linking agent.

8. A composition for oral delivery of a substance or substances to the circulation or lymphatic drainage system of a host, comprising at least one complex according to claim 1.

9. A composition according to claim 8, further comprising a physiologically acceptable carrier, diluent, excipient or adjuvant.

10. A composition for oral delivery of a substance to the circulation or lymphatic drainage system of a host, comprising a complex of claim 1, together with a physiologically acceptable carrier, diluent, excipient or adjuvant.

11. A composition according to claim 9 or 10, wherein the carrier, diluent, excipient or adjuvant is orally and pharmaceutically acceptable.

12. A method of orally delivering a substance to the circulation or lymphatic drainage system of a host requiring such substance, comprising:

orally administering to the host an effective amount of a complex according to claim 1.

13. A method of orally delivering a substance to the circulation or lymphatic drainage system of a host requiring such substance, comprising:

orally administering to the host an effective amount of a complex according to claim 2.

14. A method according to claim 12, wherein the host is a vertebrate.

15. A method according to claim 12, wherein said complex comprises a compound selected from the group consisting of a hormone, drug, immunogen, DNA or RNA.

* * * * *